United States Patent [19]
Kimura et al.

[11] Patent Number: 5,333,487
[45] Date of Patent: Aug. 2, 1994

[54] SPARK-EXCITED FLUORESCENCE SENSOR

[75] Inventors: Hiroshi Kimura, Northridge; Tetsuo Hadeishi, deceased, late of Kensington, by Chikako Hadeishi, Administrator; Harold M. Olsen, W. Covina; Chan S. Bak, Newberry Park, all of Calif.

[73] Assignee: Hughes Aircraft Company, Los Angeles, Calif.

[21] Appl. No.: 793,052

[22] Filed: Nov. 15, 1991

[51] Int. Cl.$^5$ ............................................. G01N 30/02
[52] U.S. Cl. ................................... 73/23.31; 356/313; 73/1 G
[58] Field of Search ............... 73/1 G, 23.31, 23.32; 356/313, 311, 306, 417; 60/276

[56] References Cited

U.S. PATENT DOCUMENTS

| | | | |
|---|---|---|---|
| 2,436,104 | 2/1948 | Fisher et al. | 356/306 |
| 3,547,541 | 12/1970 | Varnela | 356/306 |
| 3,819,945 | 6/1974 | Egan et al. | 356/306 |
| 3,998,095 | 12/1976 | Tinkham et al. | 73/23.31 |
| 4,255,051 | 3/1981 | Imamura et al. | 356/313 |
| 4,466,943 | 8/1984 | Murase et al. | 356/315 |
| 4,611,562 | 9/1986 | Nakano et al. | 73/23.32 |
| 4,692,875 | 9/1987 | Riley et al. | 356/313 |
| 4,766,318 | 8/1988 | Adler-Golden et al. | 356/313 |
| 4,857,275 | 8/1989 | Furusaki et al. | 73/23.32 |
| 5,085,499 | 2/1992 | Griffin et al. | 356/313 |
| 5,093,553 | 3/1992 | Harvey et al. | 356/313 |
| 5,125,746 | 6/1992 | Sayegh et al. | 356/417 |
| 5,153,673 | 10/1992 | Amirav | 356/417 |

FOREIGN PATENT DOCUMENTS 0192919  9/1986  European Pat. Off. .

Primary Examiner—Robert Raevis
Attorney, Agent, or Firm—V. D. Duraiswamy; W. K. Denson-Low

[57] ABSTRACT

A spark-excited fluorescence sensor (10) is provided which enables monitoring of various gas species (14), such as $H_2$, $CO_x$, $NO_x$, $N_2$, $NH_x$ and hydrocarbons added to a system as source fuels and/or additive agents, or discharged from a system as exhaust including pollutants, for more efficient use of fuels for optimizing performance of the system, and, also, for reducing pollutants in the atmosphere. The spark-excited fluorescence sensor of the invention comprises a spark plug (12) to excite molecules of the gaseous species, an optical fiber window (18) and an optical fiber bundle (20) to collect and transmit, respectively, the fluorescence, bandpass filters (24) to select predetermined wavelengths corresponding to the gases to be detected, detectors (26), and signal processor (28). The output from the signal processor is then used to improve overall performance of the system.

11 Claims, 4 Drawing Sheets

CARBON MONOXIDE

NITROGEN

METHANE

OXYGEN

SPARK-EXCITED FLUORESCENCE SENSOR

BACKGROUND OF THE INVENTION

1. Field of the Invention

The present invention relates to the monitoring of gas species as atmospheric pollutants, and also as source fuels, additive agents and emissions of various systems and to improve the operating efficiency of the various systems.

2. Description of Related

Monitoring of intake and output gases of systems, such as, but not limited to, fuel cells, smoke stacks, burn-boxes, fume hoods, and particular, internal combustion systems and sources of pollution would allow the efficient use of fuels and the control and reduction of pollution discharged into the atmosphere. Unfortunately, although there are solid state sensors to monitor individual gases, such as NO, CO, $H_2O$, their response times are too long to enable monitoring instantaneous variations in the concentrations of the gas species to provide feedback for control. Also, these prior art sensors tend to suffer from poisoning by various gas molecules in the exhaust.

Thus, there is a need for a reliable sensor which can monitor and control systems which use and discharge various gaseous species with a fast response time.

SUMMARY OF THE INVENTION

In accordance with the invention, a spark-excited fluorescence sensor is provided, which enables monitoring of various intake and output gas species of the above-mentioned systems. The sensor according to the invention is particularly sensitive to various gas species, such as $H_2$, $CO_x$, $NO_x$, $O_2$, $N_2$, $NH_x$, hydrocarbons and additive agents. The monitoring by the sensor provides more efficient use of gases as fuel sources, optimization of performance and, also, can be used, in conjunction with associated controls, to reduce pollutants discharged into the environment.

The spark-excited fluorescence sensor of the invention comprises:

(a) excitation means to excite molecules of the various gas species from a ground state to excited states, whereby the molecules in the excited state emit fluorescence upon decay to the ground state;

(b) an optical collection means to collect the fluorescence emitted;

(c) an optical transmission means to transmit the collected fluorescence as an optical signal;

(d) filter means to select pre-determined bands of wavelengths corresponding to the gaseous species to be detected;

(e) detection means for converting the optical signals to corresponding electrical signals; and (f) signal processing means to provide output signals corresponding to the concentration of each gaseous species detected.

A method for monitoring various gaseous species is also provided.

DESCRIPTION OF THE PREFERRED EMBODIMENTS

Figure 1:
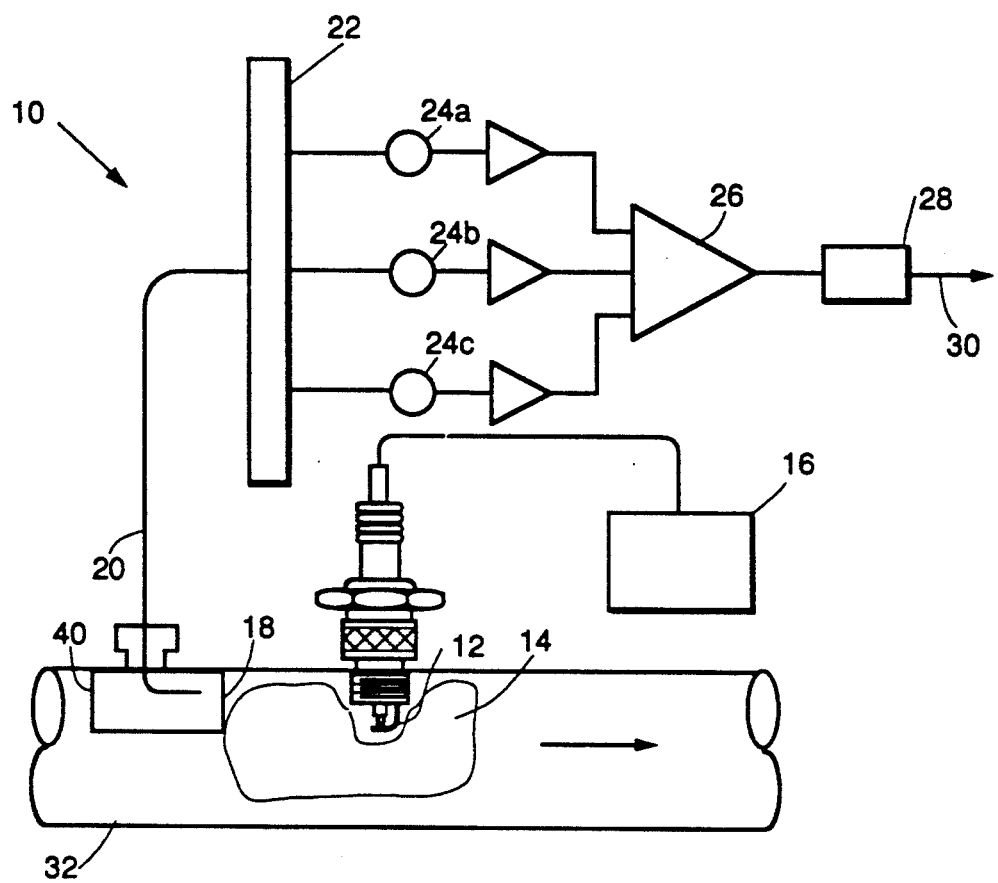
FIG. 1 is a schematic diagram of a spark-excited fluorescence sensor of the invention.

Referring now to FIG. 1, there is shown a spark-excited fluorescence sensor 10 of the invention, which comprises means 12 to excite molecules, shown generally at 14. An excitation source 16 is used to activate the excitation means 12.

Molecules excited from a ground state to upper excited states emit fluorescent light upon decay to the ground state. This fluorescent light is at a wavelength that is unique and characteristic for each molecule.

A light collection means 18 and a light transmissive means 20 permit the fluorescence generated by the excitation means 12 to be collected and transmitted, respectively, to a plurality of bandpass filters 22 for selecting out undesired wavelengths and for permitting only pre-selected wavelengths to pass through to a plurality of detectors 24. In this manner, only those fluorescent energies associated with particular molecules are detected, each by its own detector. For example, the bandpass filters 22 could each be set to pass through fluorescent energies associated with one of the species of CO, NO, and $CH_4$. The energy associated with that species is then detected by one of the detectors, 24a, 24b, 24c. While three detectors are shown, there is no limit to the number of detectors that may be employed, each set to detect the fluorescent energy associated with a particular gaseous species.

The signal from each detector 24 is then amplified by an amplifier 26, and the amplified signal is subjected to further signal processing by processing means 28 to provide an output 30, such as a real-time indication of the quantities of various intake/output gases and/or pollutants for making adjustments in the system.

In the present invention, gas species added to or discharged from the system, such as fuel cells, smoke stacks, burn-boxes, fume hoods, and in particular, internal combustion systems and sources of pollution, are excited by the spark discharge from the ground state to the excited states. Intensities of the fluorescence emitted at certain frequencies, when molecules, atoms, or ions relax to their ground state, are proportional to the concentrations of the species. By selecting a high oscillator-strength band whose intensity is proportional to the concentrations, and is free from interferences and quenching, then concentrations can be determined with good sensitivity.

Figure 2:
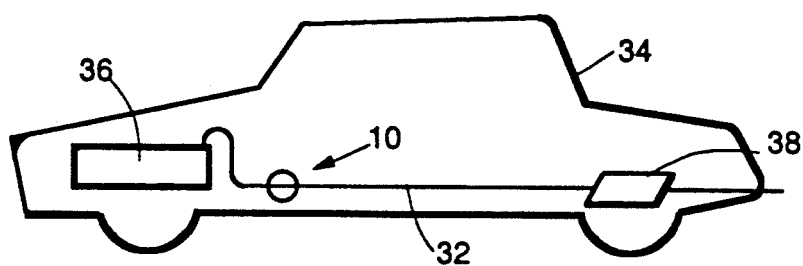
FIG. 2 is a schematic diagram depicting use of the sensor of the invention in an automobile.

In practice, as shown in a preferred embodiment in FIG. 2, the spark plug 12 and light collection and transmissive means 18, 20 are installed in the exhaust pipe 32 of the automobile 34 at a location where the combustion of the exhaust is representative of the combustion products before the occurrence of decomposition, association, or disproportionation of the gas species. In particular, the sensor 10 is inserted in the exhaust pipe 32 between the engine 36 and the catalytic converter 38. The excitation source 16 for activating the spark plug 12 is conventional.

The light collection means, preferably an optical fiber window, 18 is installed near the spark plug 12 to collect the fluorescence. The fiber optic window is encased in a guard housing 40 to protect against mechanical damage and is shielded from deposition of foreign particles.

The light transmissive means, preferably a fiber optic bundle, 20 is connected to the window 18 to transmit the fluorescences to bandpass filters 22.

The bandpass filters 22 are chosen to transmit only the selected fluorescence bands. For each of the bandpass filters 22, an optical detector 24 is interfaced to convert the optical signals to electrical signals.

The electrical signals are amplified, if necessary, by amplifier 26 and transmitted to the signal processor 28, where they are converted to concentrations. Because of the dependency of fluorescence intensity on excitation energy, an internal standard must be chosen to accurately determine the concentrations of the molecules. The use of a standard also monitors, and compensates for, the attenuation of light due to changes in the surface condition of the window 18. The internal standard is selected from molecules in the exhaust gas whose concentrations are relatively constant, independent of the combustion process; $N_2$ is a good candidate.

The concentration of a species is determined relative to the concentration of the internal standard. The signals are used to control the efficient operation of the system, or for example, the combustion conditions for a more efficient combustion or to reduce pollutants.

Figure 3:
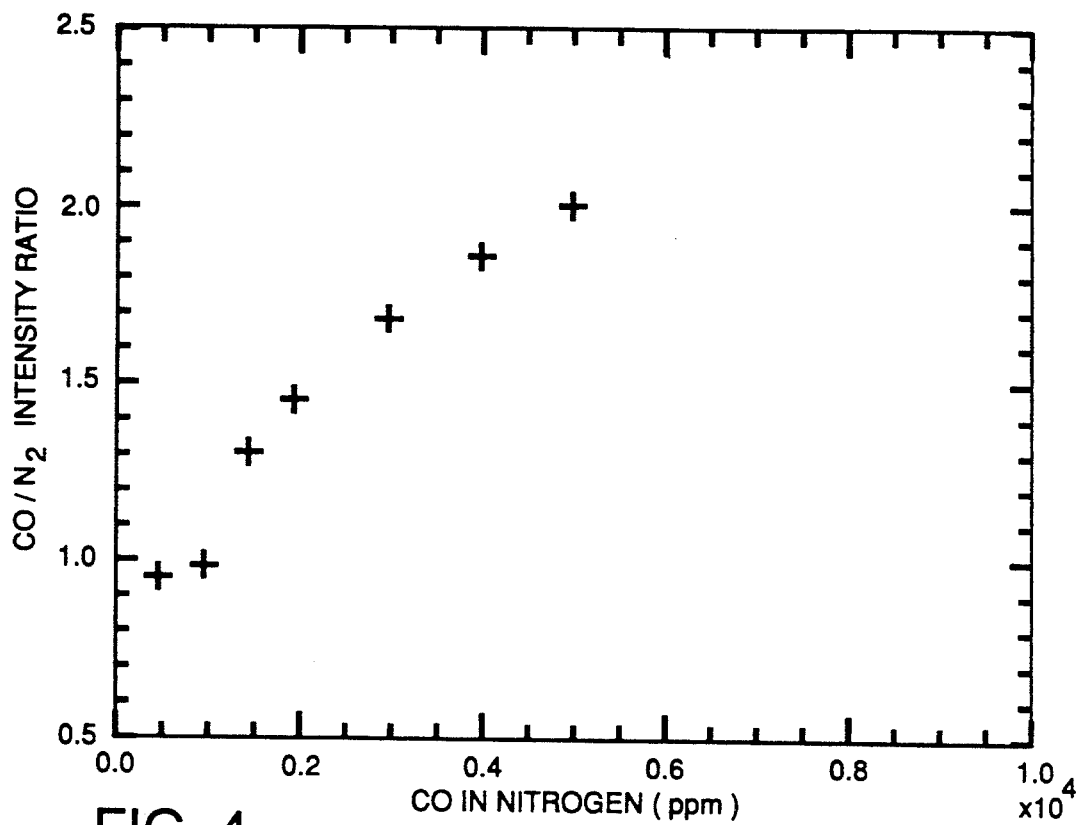
FIG. 3, on coordinates of intensity ratio and concentration in parts per million, is a calibration plot of the ratio of the fluorescence intensity of CO to $N_2$ as a function of concentration of CO in $N_2$.
Figure 4:
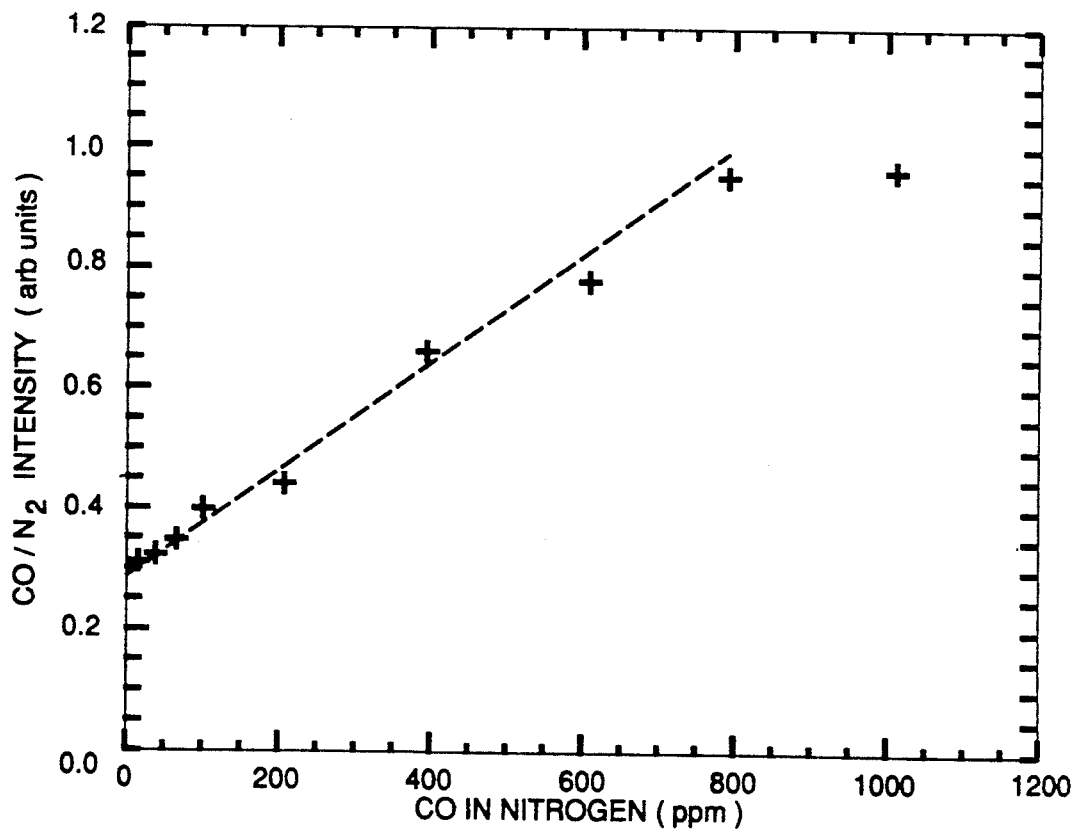
FIG. 4 is a calibration plot similar to that of FIG. 3, but at lower CO concentrations.
Figure 5A:
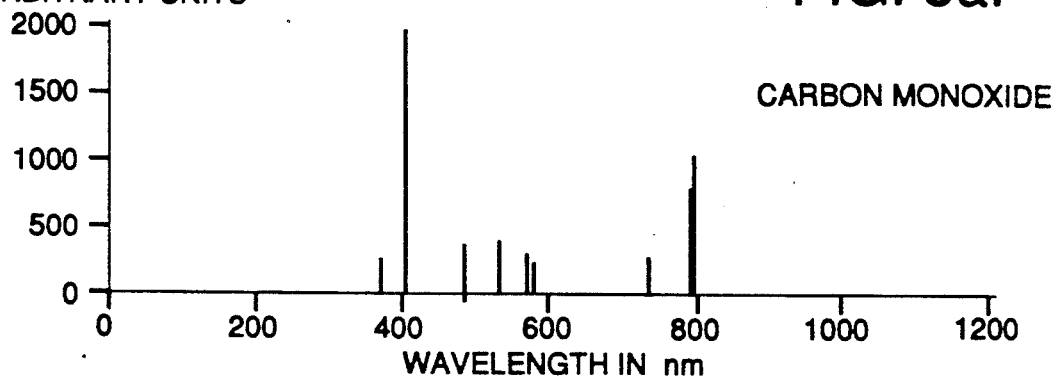
FIGS. 5a–d, on coordinates of intensity (in arbitrary units) and wavelength (in nm) are spectra showing the positions of fluorescence bands in CO (FIG. 5a), $N_2$ (FIG. 5b), $CH_4$ (FIG. 5c), and $O_2$ (FIG. 5d)
Figure 5B:
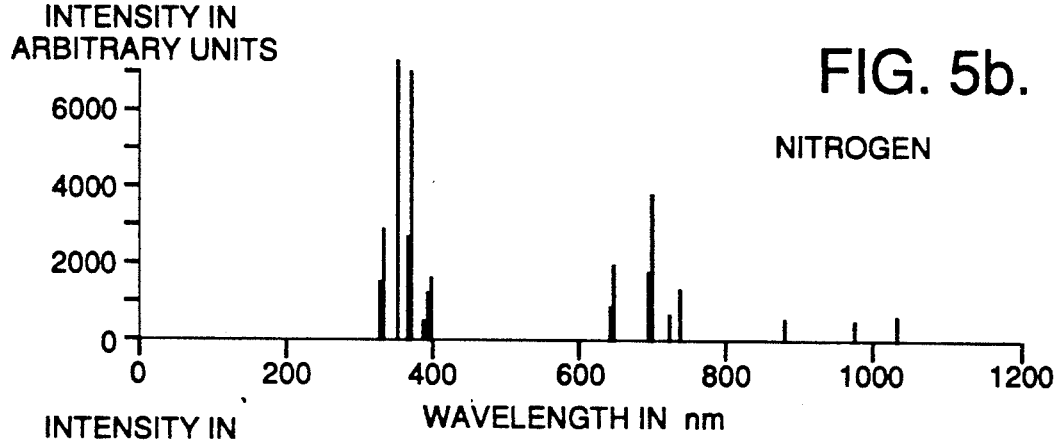
Figure 5C:
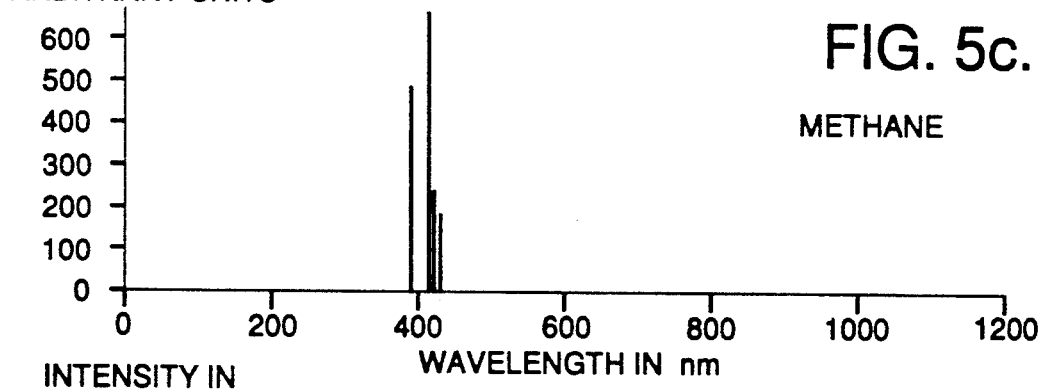
Figure 5D:
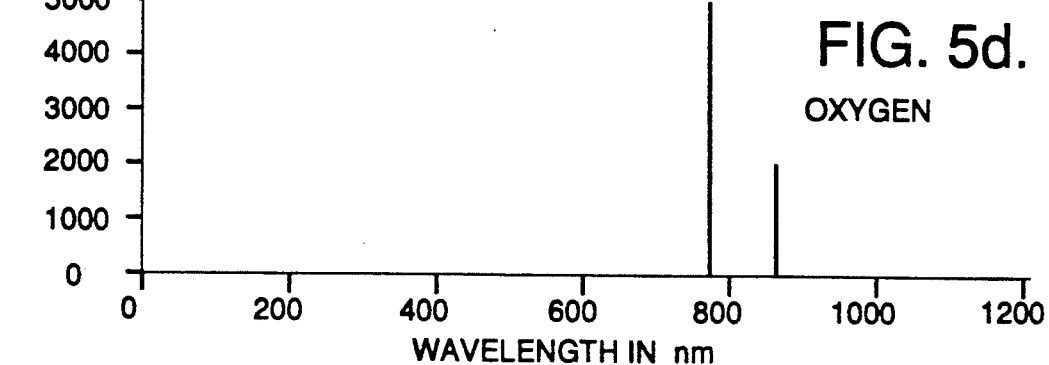

FIG. 3 is a calibration plot of the fluorescence intensity ratio, $I(CO)/I(N_2)$ as a function of the concentration of CO in $N_2$ (in ppm). This plot, which was obtained from apparatus substantially identical to that shown in FIG. 1, provides calibration of CO as a function of concentration, and shows that the system behaves in a monotonic fashion. In FIG. 4, the calibration of CO in $N_2$ represented by FIG. 3 is extended to lower concentrations.

Advantageously, the fluorescence spectra for carbon monoxide, nitrogen, methane, and oxygen have high intensity bands at sufficiently different wavelengths to provide a choice of selection. FIGS. 5a–d show the positions in wavelength of fluorescence bands and their intensities in arbitrary units for CO, $N_2$, $CH_4$, and $O_2$. Any one of the bands free of interferences from other gases in the automobile exhaust emissions may be selected for monitoring. For example, in the case of a gas mixture where CO, $CH_4$, and $N_2$ are present, the band at approximately 800 nm must be chosen for CO analysis. For $CH_4$, a narrow bandpass filter must be employed to avoid interferences from CO and $N_2$.

Also, the relative concentrations of gases in the mixture must be considered for the selection of the band. The fluorescence intensities as shown in FIGS. 5a–d are for pure gases. In the dilute state, the relative intensities may vary widely between gases, and, therefore, the sensitivity of each band must be determined.

Figure 6:
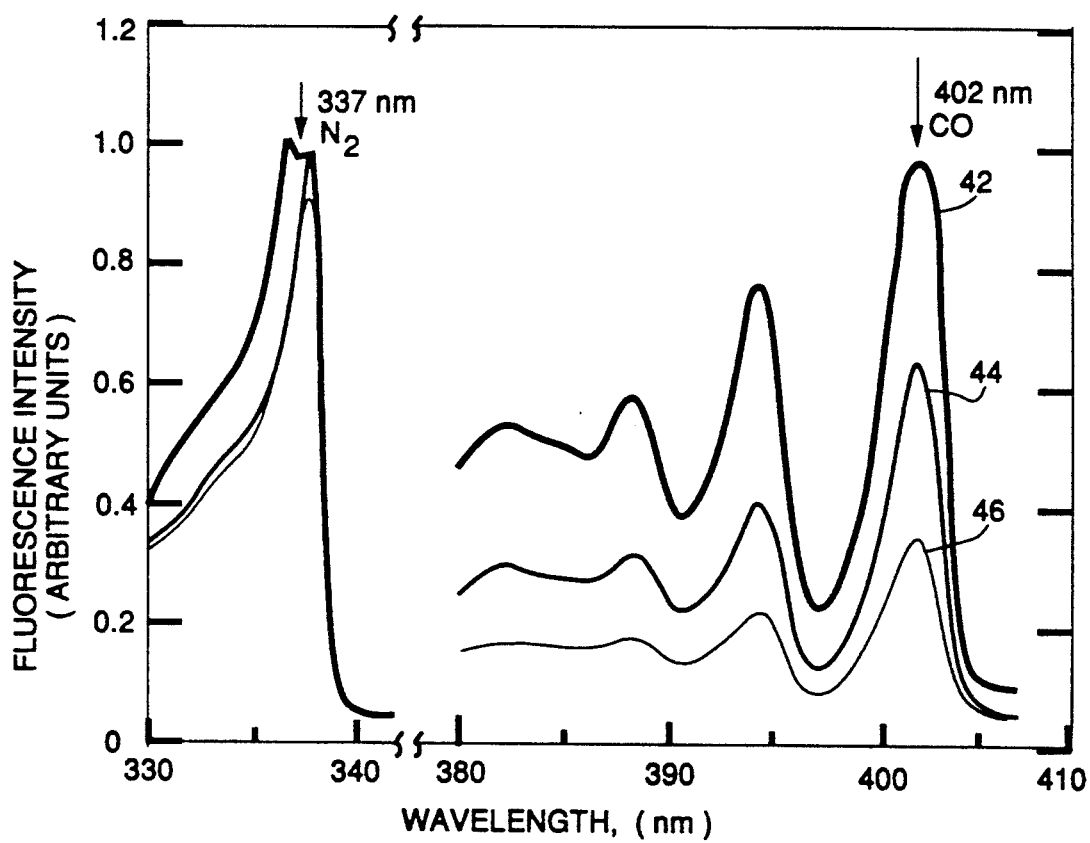
FIG. 6, on coordinates of intensity and wavelength in nm, is a plot of the fluorescence intensity of CO in $N_2$ as a function of wavelength.

It is evident from FIGS. 5a–d that there is a strong band for CO at about 400 nm that is suitably employed in the practice of the invention. FIG. 6 shows that the CO peak, at about 400 nm, varies proportionally with concentration, as shown in the Table below.

| Curve | PPM CO in $N_2$ |
|---|---|
| 42 | 800 |
| 44 | 400 |
| 46 | 100 |

Band selection for the determination of concentrations of molecules in the atmosphere or in the exhaust from internal combustion engines is as follows: For the determination of CO concentration in the absence of $CH_4$ or when the concentration of $CH_4$ is low relative to CO, the fluorescent band at approximately 402 nm is selected. This band is highly sensitive and does not exhibit saturation in a wide o concentration range as shown in FIGS. 3 and 4; concentrations as low as 20 ppm and as high as 10,000 ppm (1%) can be measured by this technique. For $N_2$, the internal standard, the band at approximately 337 nm is selected. For the determination of concentrations of multiple chemical species, their fluorescence intensities are normalized to that of the internal standard, $N_2$. For the determination of nitric oxide, NO, the band at 872 nm, which is free of interferences from other molecules, is selected. This band is, also, calibrated and shows that concentrations in a wide range, from 20 to 10,000 ppm, are measurable.

From the information in FIG. 6, it is seen that it is important to normalize the data to $N_2$, as is done in FIGS. 3 and 4, since the spark intensity varies. For CO analysis in the absence of $CH_4$, two optical bandpass filters, one for the CO band at about 400 nm and the other for the $N_2$ band at about 337 nm, and two detectors 24a, 24b are required to quantitatively determine the concentration of CO. In determining the concentration, the signal from the detector for CO is divided by that from the detector for $N_2$ by the signal processor 28, and the ratio is converted to concentration by a calibration curve, such as the one shown in FIG. 3, installed in the processor.

More specifically, the conversion of optical signals to concentrations of gaseous species is achieved by the following processes:

1. The optical signals (the fluorescence) of gases are transmitted by optical fibers 20 to the bandpass filters 22, where only the selected band is transmitted to the photodetectors 24.

2. The photodetectors 24 convert the optical signals to electrical signals, which are amplified by the amplifier 26 and then transmitted to the microprocessor 28.

3. The microprocessor 28 takes the electrical signal of each species and normalizes it with the signal of the N2 gas, for example.

4. The normalized intensity of each species is then converted to concentration by the calibration curve installed in the microprocessor. For examples of calibration curves, see FIGS. 3 and 4. The installation of calibration curves in microprocessors is well-known and does not form a part of this invention.

5. The concentration signals are transmitted to the main computer, which is programmed to provide instructions via output 30 to optimize the monitored system. The instructions include, but are not limited to, sending an alarm signal or shutting down the system when concentrations reach a certain level; providing a warning indicator signal to replace a failed component, such as the catalytic converter; adjusting the intake gas levels which are monitored by the invention in a feedback loop with the analysis of the output gas levels; and adjusting fuel/air mixture ratios. All of these actions provide optimum operation of the systems for efficient use of fuels and reduction of pollutants.

The data supporting the present application were accumulated on a test apparatus, analogous to that depicted in FIG. 1, comprising a conventional spark plug, such as AC, Bosch, or NGK, using a conventional distributor module and coil from a 1990 model Chevrolet S-10 pickup in a 6 cylinder, 4.3 liter engine. The pick up coil in the distributor, which was driven mechanically, was replaced with a pulse generator through a pulse transformer. Using a maximum red-line speed of 6,000 rpm engine speed, the coil fired at 600 times/sec. The test set could be varied to fire from 5 times/sec to 4,000 times/sec. The data herein was collected at 500 cps (times/sec). The battery connection to the automobile coil was replaced with a 12 volt DC power supply.

A test chamber replaced the actual environment, such as the exhaust pipe in the automobile. A gas inlet and gas outlet capability were included, as well as a heater element to simulate exhaust gas temperatures. As the test gases passed the excited spark plug, optical emission spectra were seen by a monochromator via a fiber optic window (Suprasil) and either an optical lens or an optical fiber. The window did not absorb the optical wavelengths of the spectra under study. The spectral beam could then be concentrated by using the optical lens or the fiber optic cable to transmit the optical signal to the monochromator. Data from the monochromator was then fed to a computer for analysis and calibration.

Thus, there has been disclosed a spark-excited fluorescence detector for detecting gaseous species in various systems. Although the embodiment described was an automobile exhaust system, the invention should not be limited thereto and the invention is intended to apply to many systems which use and/or discharge gaseous species during operation, such as fuel cells, smoke stacks, remediation systems, and internal combustion systems generally. It will be appreciated that various changes and modifications of an obvious nature may be made without departing from the spirit of the invention. For example, the invention may include a chamber to sample the gases in a smoke stack and provide the sample to the excitation means.

The invention may include monitoring gaseous levels of additive agents, such as ammonia, added to a remediation system to react with $NO_x$, to reduce $NO_x$ in the atmosphere. A feedback loop between intake additive level and the output additive level and $NO_x$ level provides constant monitoring at both ends. The molecules of the additive agent that are excited have characteristic fluorescence at wavelengths which are determined in the same way as described above for the other gaseous species. The invention senses a characteristic wavelength or band with an appropriate bandpass filter, as described above. These and other such changes and modifications are considered to fall within the scope of the invention as defined by the appended claims.

What is claimed is:

1. A spark-excited flourescence sensor for detecting at least one gaseous species in vehicular exhaust gas flowing in an exhaust pipe of a vehicle, comprising:
   (a) a spark plug to excite molecules in said vehicular exhaust gas from a ground state to excited states, whereby said molecules in said excited states emit fluorescence upon decay to said ground state, said spark plug installed in a portion of said exhaust pipe;
   (b) a guard housing provided with an optical fiber window to collect said fluorescence emitted, said guard housing installed in a portion of said exhaust pipe and positioned to receive said fluorescence generated by said spark plug through said optical fiber window;
   (c) an optical fiber bundle to transmit said collected fluorescence as an optical signal, a portion of said fiber optic bundle installed in said guard housing and positioned to receive said fluorescence transmitted through said optical fiber window;
   (d) a plurality of bandpass filters, each bandpass filter set to pass a unique band associated with a pre-determined gaseous species and adapted to receive said optical signal from said optical fiber bundle;
   (e) a plurality of detectors for converting said optical signals to corresponding electrical signals, each detector operatively associated with one of said bandpass filter; and
   (f) signal processing means to provide output signals corresponding to the concentration of each gaseous species detected.

2. The sensor of claim 1 further including amplification means to amplify said electrical signals from said detection means.

3. The sensor of claim 1 wherein said filter means includes a bandpass filter set to select about 402 nm as said pre-determined band for analysis of CO substantially free of $CH_4$.

4. The sensor of claim 1 wherein said filter means includes a bandpass filter set to select about 872 nm as said pre-determined band for analysis of NO.

5. The sensor of claim 1 wherein said filter means includes a second bandpass filter for the internal standard $N_2$ band at about 337 nm.

6. The sensor of claim 5 wherein said signal processing means normalizes the optical signal from each said gaseous species with respect to the optical signal from $N_2$ to provide a normalized intensity for each said gaseous species and then converts the normalized intensity to concentration by means of a calibration curve installed in said signal processing means.

7. A method for monitoring various gaseous species in vehicular exhaust gas flowing through an exhaust pipe to generate information for providing a more efficient engine performance, comprising:
   (a) exciting said various gaseous species in said exhaust pipe from a ground state to excited states, whereby said molecules in said excited states emit fluorescence upon decay to said ground state;
   (b) collecting said fluorescence emitted;
   (c) transmitting said collected fluorescence as an optical signal;
   (d) selecting pre-determined bands of wavelengths corresponding to said gaseous species to be detected;
   (e) detecting said pre-determined bands of wavelengths and converting said optical signals to corresponding electrical signals; and
   (f) processing said electrical signals to provide output signals corresponding to the concentration of each gaseous species detected.

8. The method of claim 7 wherein a gas comprising CO substantially free of $CH_4$ is detected by selecting as said pre-determined band about 402 nm.

9. The method of claim 7 wherein a gas comprising NO is detected by selecting as said pre-determined band about 872 nm.

10. The method of claim 7 wherein $N_2$ is used as an internal standard and is detected by selecting as said pre-determined band about 337 nm.

11. The method of claim 10 wherein said signal processing means normalizes the optical signal from each said gaseous species with respect to the optical signal from $N_2$ to provide a normalized intensity for each said gaseous species and then converts the normalized intensity to concentration by means of a calibration curve installed in said signal processing means.

* * * * *